US007713736B2

(12) United States Patent
Beebe et al.

(10) Patent No.: US 7,713,736 B2
(45) Date of Patent: May 11, 2010

(54) CELL MIMIC PLATFORM AND METHOD

(75) Inventors: David J. Beebe, Monona, WI (US); Jaisree Moorthy, Madison, WI (US); Richard R. Burgess, Madison, WI (US)

(73) Assignee: Wisconsin Alumni Research Foundation, Madison, WI (US)

( * ) Notice: Subject to any disclaimer, the term of this patent is extended or adjusted under 35 U.S.C. 154(b) by 539 days.

(21) Appl. No.: 10/997,259

(22) Filed: Nov. 24, 2004

(65) Prior Publication Data

US 2006/0110722 A1 May 25, 2006

(51) Int. Cl.
*C12N 5/00* (2006.01)
(52) U.S. Cl. .................... 435/325; 422/68.1; 422/82.07
(58) Field of Classification Search ....................... None
See application file for complete search history.

(56) References Cited

U.S. PATENT DOCUMENTS 6,488,872 B1 * 12/2002 Beebe et al. .................. 264/31

OTHER PUBLICATIONS

Beebe et al. , Annu. Rev. Biomed. Eng., 2002, vol. 4, p. 261-286.*

Eddington et al., Advanced Drug Delivery Review, Feb. 2004, vol. 56, p. 199-210.*

Whitesides, G. M.,, Nature Biotechnology, Oct. 2003, vol. 21, No. 10. p. 1161-1165.*

Beebe et al., Annu. Rev. Biomed. Eng., 2002, vol. 4, p. 261-286.*

Khandurina et al., Current Opinions in Chemical Biology, 2002, vol. 6, p. 359-366.*

* cited by examiner

*Primary Examiner*—L Blaine Lankford
*Assistant Examiner*—Kade Ariani
(74) *Attorney, Agent, or Firm*—Boyle Fredrickson, S.C.

(57) ABSTRACT

A platform and method for mimicking the environment within a cell is provided. The platform includes a microfluidic device defining a chamber. At least one hydrogel post is positioned within the chamber of the microfluidic device. Each hydrogel post defines a corresponding pore for receiving a first molecule therein. Second molecules are introduced into the pores of the hydrogel posts and the interactions between the first and second molecules are observed.

7 Claims, 4 Drawing Sheets

FIG. 5
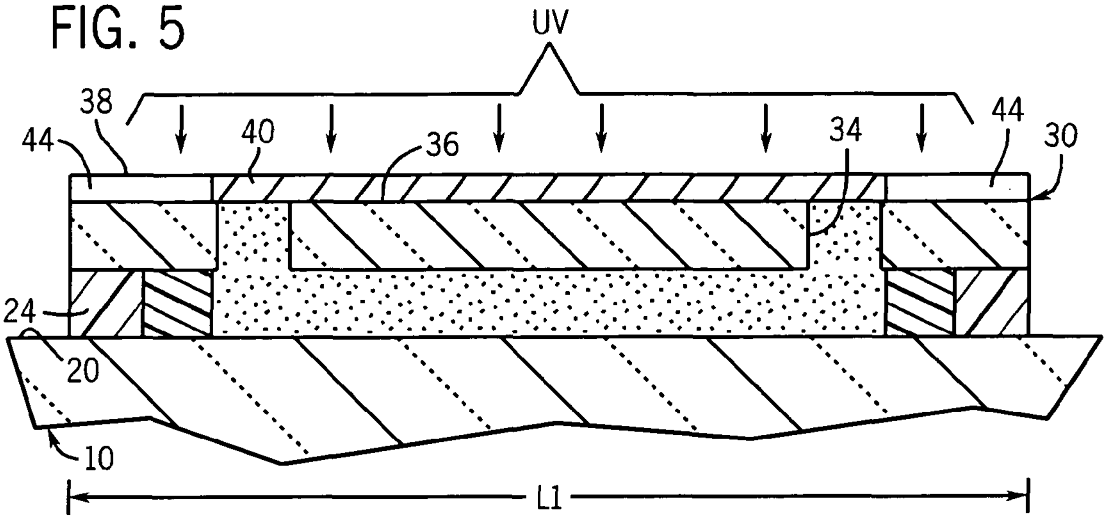
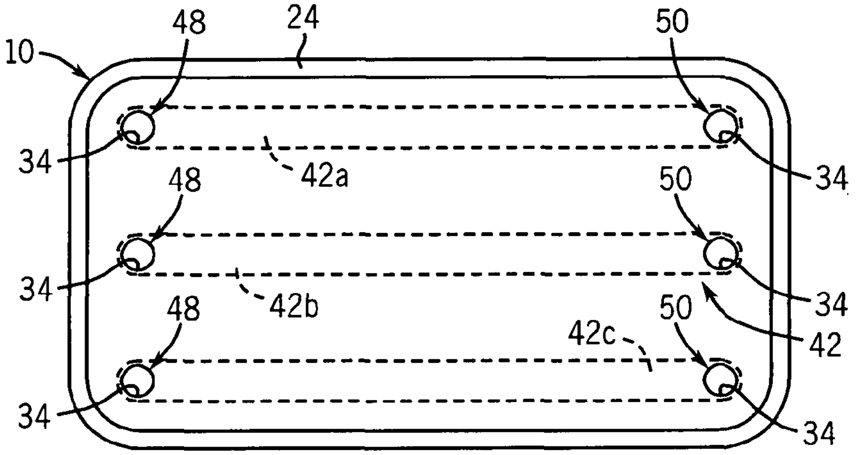
FIG. 6
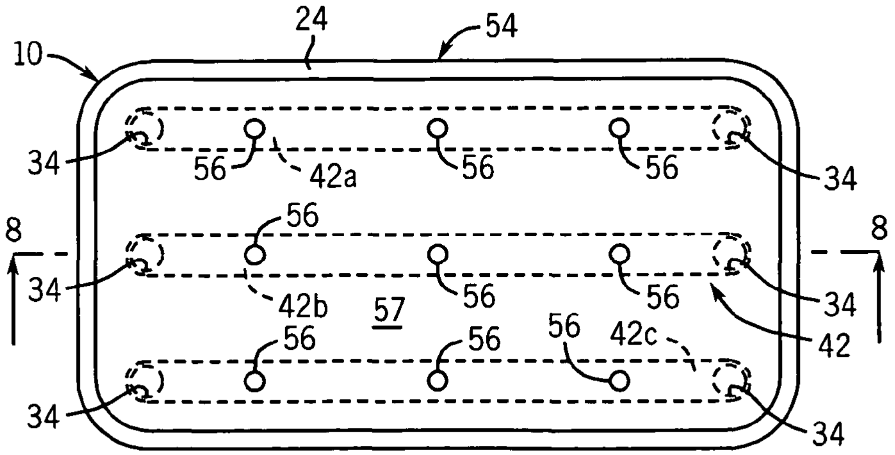
FIG. 7

FIG. 8
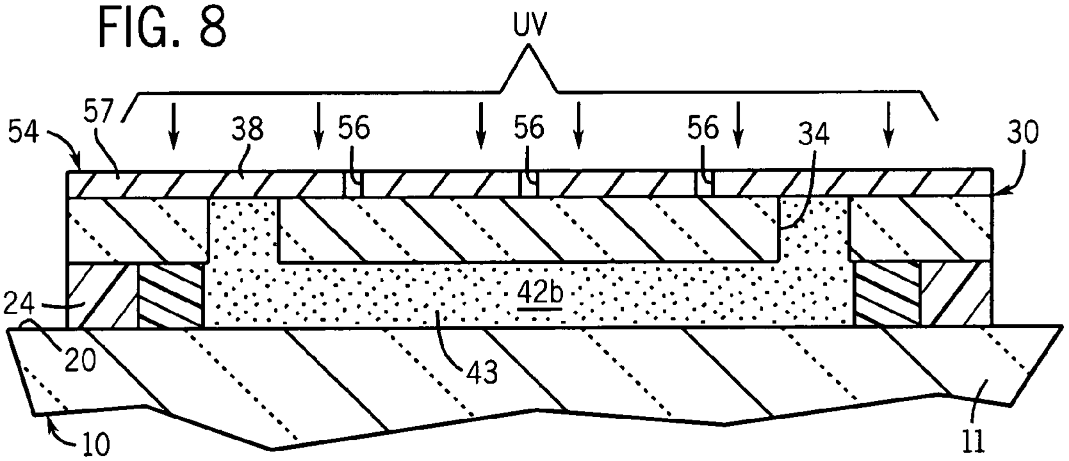
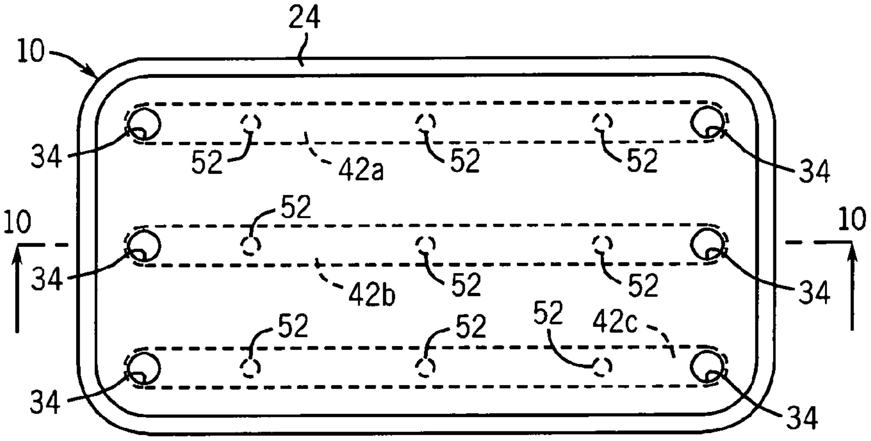
FIG. 9
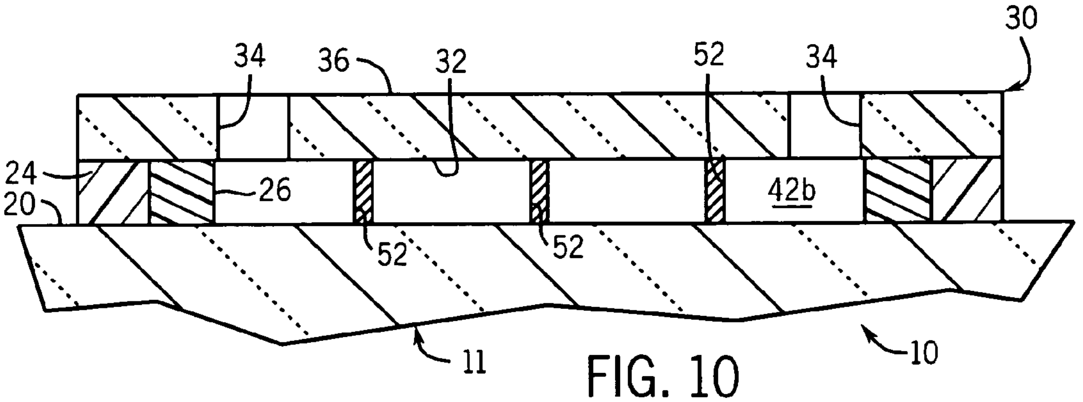
FIG. 10

CELL MIMIC PLATFORM AND METHOD

REFERENCE TO GOVERNMENT GRANT

This invention was made with United States government support awarded by the following agencies: DOD ARPA F 30602-00-2-0570. The United States has certain rights in this invention.

FIELD OF THE INVENTION

This invention relates generally to microfluidic devices, and in particular, to microfluidic-based cell mimic platform for biomolecular studies and a method of mimicking the environment within a cell utilizing the platform.

BACKGROUND AND SUMMARY OF THE INVENTION

The various events that occur inside a cell, such as metabolism and signal transduction, are orchestrated at the molecular level. For example, in signal transduction, a cascade of biomolecular interactions is initiated. These interactions include (but are not limited to) phosphorylation, binding and transportation of molecules. The effects of these interactions are often transmitted to the nucleus wherein the gene expression pattern is modified based on the signal. In metabolism (e.g., glycolysis), many enzymatic steps occur in sequence. Moreover, activation of enzymes is often controlled by interaction of the enzymes with other molecules (activators). Thus, these enzymatic steps also involve synchronization in terms of movement of molecules, binding and chemical modification.

A cell contains a large number of macromolecules (proteins, nucleic acids, polysaccharides), small molecules (glucose), ions and water. A cell also contains a network of protein filaments, referred to as the cytoskeleton, which is involved in a number of cell processes, in addition to providing mechanical support and defining the structure of the cell. The cytoskeleton is formed from protein filaments (e.g., actin). It can be appreciated that accommodating all these materials in a small volume results in a crowded environment within the cell. Moreover, the protein filaments create confined volumes (or compartments) inside the cell.

In order to study the transportation of molecules inside the cell and organelles such as mitochondria, fluorescent-based experiments have been performed. In these experiments, fluorescent probes (e.g., dextrans or ficolls) are micro-injected into the cytoplasm and the diffusion is studied by measuring the time taken for recovery of fluorescence after photo-bleaching a small area. These experiments reveal that for non-interacting probes (e.g., dextran), transportation is progressively diminished as the molecular weight of the probe is increased. Based on these observations, researchers describe the environment inside the cytoplasm to be "sieving." This effect is thought to be largely caused by the structure of the cytoskeleton. For probes or molecules that can interact with biomolecules inside the cytoplasm (e.g., DNA), the mobility is more complex. The interaction with molecules leads to "traps" whose strength is related to the specificity of the interaction; i.e., stronger interaction leads to bigger traps. These traps or barriers result in anomalies in diffusion that have been observed both in cytoplasm and in organelles. Moreover, when the cell is depleted of Adenosine Triphoshate (ATP), the mobility of glycolytic enzyme is reduced; thus suggesting that mobility of molecules is affected by the metabolic state of the cell. A common observation of the cytoplasm environment is that the degree of crowding is not consistent. Diffusion of non-interacting probes indicates that certain regions are densely packed compared to other regions. Furthermore, it has been reported that the density of actin filaments (part of the cytoskeleton) is dynamic.

Currently, most biochemical interactions are studied in solution phase wherein the concentration of the molecules is dilute. Given the complexity of the cellular environment, comparing results from dilute solution studies to the actual interactions inside the cell is difficult. For example, side effects of drugs that are designed to interact with specific biomolecules in solution phase may be a result of variations in interaction due to the different environment in the cell. On the other extreme, studies performed inside cells are often difficult to characterize due to multiplicity of interactions and variations between cells. Therefore, there exists a need for a model environment that is simpler than cells yet captures the basic characteristics of the cellular nano-environment such as the presence of charge, crowding, water content and structure. It can be appreciated that such a model environment would aid in the development of effective inhibitory molecules (e.g., drugs) and in understanding the basic mechanisms of cell signaling and behavior.

Therefore, it is a primary object and feature of the present invention to provide a microfluidic-based cell mimic platform for biomolecular studies and a method of mimicking the environment within a cell utilizing the same.

It is a further object and feature of the present invention to provide a microfluidic-based cell mimic platform and a method of mimicking the environment within a cell utilizing the same that more accurately predicts in vivo interactions via in vitro experiments than prior platforms and methods.

It is a still further object and feature of the present invention to provide a microfluidic-based cell mimic platform and a method of mimicking the environment within a cell utilizing the same that are simple and that easily capture the basic characteristics of the cellular nano-environment.

In accordance with the present invention, a platform is provided for mimicking the environment within a cell. The platform includes a microfluidic device defining a chamber and a first hydrogel post is positioned within the chamber. The first hydrogel post defines a first pore therein. A biomolecule is received in the first pore in the post.

The platform may also include a second hydrogel post within the chamber of the microfluidic device. The second hydrogel post includes a second polymer chain defining a second pore. The first pore has a first cross sectional area and the second pore has a second cross sectional area. The second cross sectional area is less than the first cross sectional area. Alternatively, the first hydrogel post may include the second pore having the second cross sectional area. The first hydrogel post may be one of an array of hydrogel posts with the chamber of the microfluidic device. Each hydrogel post of the array of hydrogel posts has a pore therein.

The first hydrogel post is formed from a plurality of cross-linked polymer chains. In addition, a crowding agent may be received in the first pore of the first hydrogel post. The crowding agent is formed from a soluble material captured in the first hydrogel post. The platform may also include a flow of reagent flowing through the chamber of the microfluidic device. The reagent interacts with the biomolecule in the first pore.

In accordance with a further aspect of the present invention, a method is provided for mimicking a nano-environment within a cell to study the interaction between molecules. The method includes the steps of providing a micro device that defines a chamber therein and positioning a first hydrogel post within the chamber of the micro device. The first hydrogel post defines a first pore therein. First and second molecules are deposited in the first pore in the first hydrogel post. Thereafter, the interaction of the first and second molecules in the first pore is observed.

The step of depositing the first molecule in the first pore in the first hydrogel post includes the step of introducing a stream of fluid having the first molecule into the chamber. The first molecule is allowed to diffuse into the first pore. It is contemplated to vary the volume of the first pore. The method includes the additional steps of fabricating the first hydrogel post from a monomer, a cross-linker and a photo-initiator and positioning a second hydrogel post within the chamber of the micro device. The second hydrogel post defines a second pore therein. In a first embodiment, the first pore has a first volume and the second pore has a second volume wherein the second volume is less than the first volume. Alternatively, the first hydrogel post defines the second pore wherein the first pore has a first volume and the second pore has a second volume. The second volume is less than the first volume. In a still further embodiment, the first hydrogel post may be one of an array of hydrogel posts in the chamber.

In accordance with a still further aspect of the present invention, a method is provided of mimicking the environment within a cell. The method includes the steps of providing a chamber and positioning a first post within the chamber. The first post defines a first pore therein. First and second molecules are deposited in the first pore. Thereafter, the interaction of the first and second molecules in the first pore are monitored.

The step of depositing the first molecule in the first pore in the first post includes the step of introducing a stream of fluid having the first molecule into the chamber. The first molecule is allowed to diffuse into the first pore. The step of depositing the second molecule in the first pore in the first post includes the step of introducing a second stream of fluid having the second molecule into the chamber. The second molecule is allowed to diffuse into the first pore. It is contemplated to vary the volume of the first pore. The method includes the additional steps of fabricating the first post from a monomer, a cross-linker and a photo-initiator and positioning a second post within the chamber of the micro device. The second post defines a second pore therein. In a first embodiment, the first pore has a first volume and the second pore has a second volume wherein the second volume is less than the first volume. Alternatively, the first post defines the second pore wherein the first pore has a first volume and the second pore has a second volume. The second volume is less than the first volume. In a still further embodiment, the first post may be one of an array of posts in the chamber.

BRIEF DESCRIPTION OF THE DRAWINGS

The drawings furnished herewith illustrate a preferred construction of the present invention in which the above advantages and features are clearly disclosed as well as others which will be readily understood from the following description of the illustrated embodiment.

In the drawings:

FIG. 5 is a cross-sectional view of the microfluidic device taken along line 5-5 of FIG. 4;

FIG. 6 is a top plan view of the microfluidic device after formation of a plurality of channels therein;

FIG. 7 is a top plan view of the microfluidic device of FIG. 6 having a second optical mask affixed to the upper surface thereof;

FIG. 8 is a cross-sectional view of the microfluidic device taken along line 8-8 of FIG. 7;

FIG. 9 is a top plan view of the microfluidic device with hydrogel posts formed in the channels thereof;

FIG. 10 is a cross-sectional view of the microfluidic device taken along line 10-10 of FIG. 9;

DETAILED DESCRIPTION OF THE INVENTION

Figure 1:
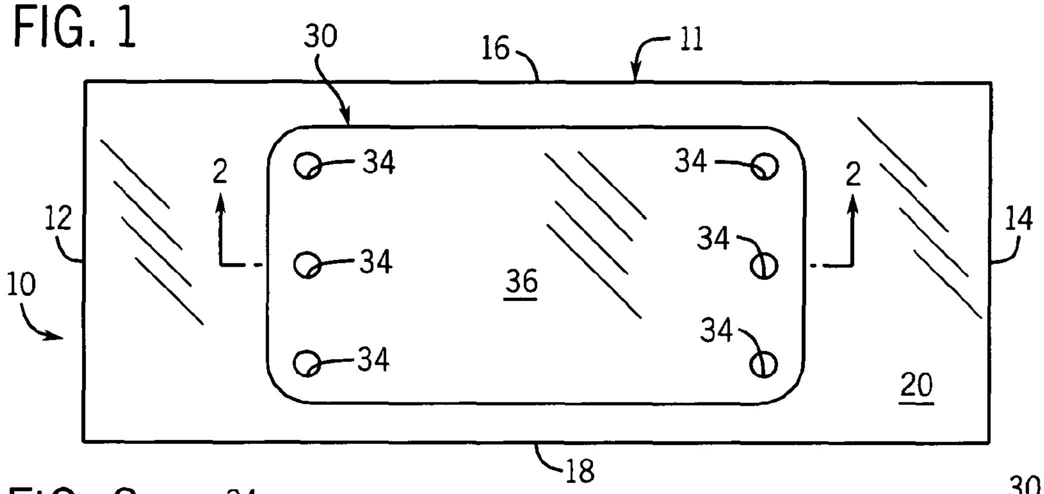
FIG. 1 is a top plan view of a microfluidic device for use in the methodology of the present invention.
Figure 2:
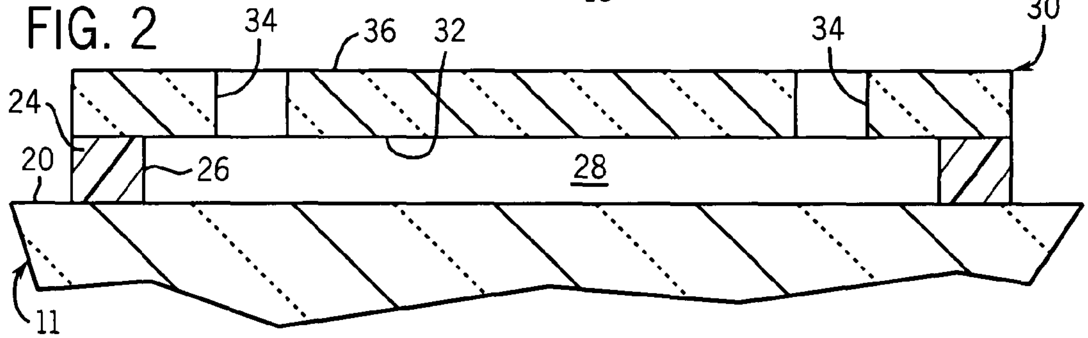
FIG. 2 is a cross-sectional view of the microfluidic device taken along line 2-2 of FIG. 1.

Referring to FIGS. 1 and 2, a microfluidic device defining the cell platform of the present invention and used to effectuate the methodology of the present invention is generally designated by the reference numeral 10. As hereinafter described, it is contemplated to fabricate a microfluidic device in a variety of manners including use of photopolymerizable solutions. It is noted, however, microfluidic device 10 may be fabricated from other materials without deviating from the scope of the present invention. Further, in order to achieve in situ fabrication of the specific components hereinafter described, liquid phase photopolymerization may be used, although the various channels within microfluidic device can be fabricated using other methods (e.g., micromolding).

By way of example, microfluidic device 10 includes a generally rectangular glass slide 11 defined by first and second ends 12 and 14, respectively; first and second edges 16 and 18, respectively; and upper face 20. Gasket 24 may take the form of a double-sided, pressure sensitive adhesive affixed to upper face 20 of glass slide 11 adjacent first and second ends 12 and 14, respectively, and first and second edges 16 and 18, respectively, thereof. Cover 30, formed from glass or a polymeric material that allows for a polymerizing agent such as ultraviolet light to pass therethrough, is positioned on gasket 24 such that inner edge 26 of gasket 24, upper face 20 of glass slide 11 and lower face 32 of cover 30 define cavity 28 within microfluidic device 10. One or more access holes 34 extend through cover 30 between upper face 36 and lower face 32 so as to allow access to the interior of cavity 28.

Figure 3:
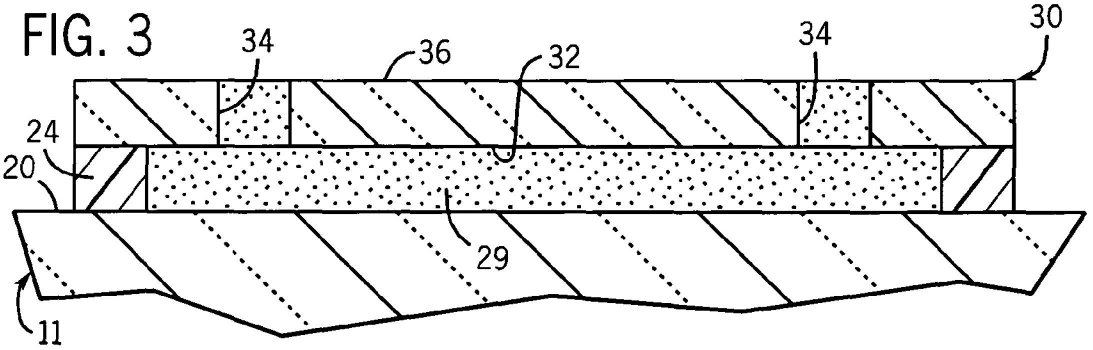
FIG. 3 is a cross-sectional view, similar to FIG. 2, showing a pre-polymer mixture within the channel of the microfluidic device.
Figure 4:
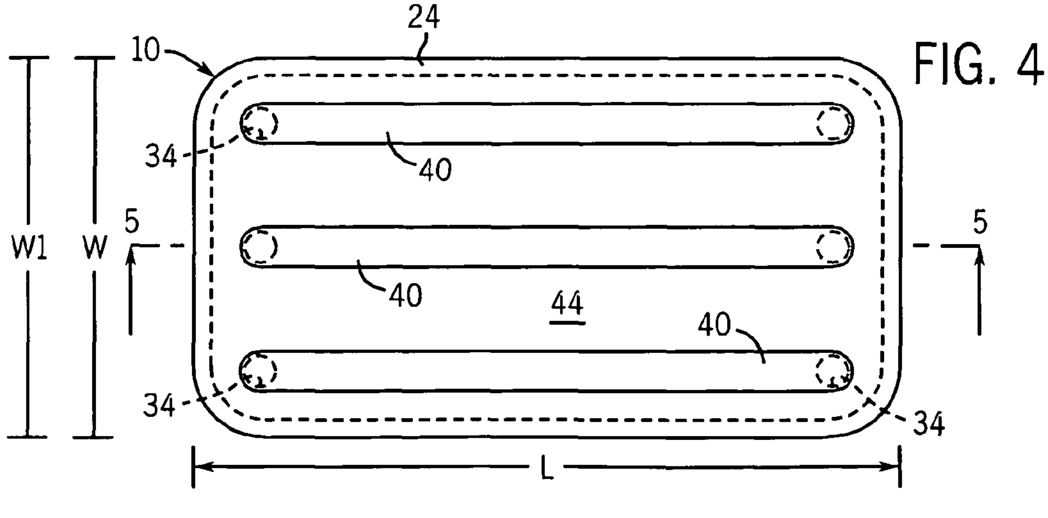
FIG. 4 is a top plan view of the microfluidic device FIG. 1 having an optical mask affixed to the upper surface thereof.

As best seen in FIG. 3, after positioning cover 30 on gasket 24, pre-polymer mixture 29 is introduced into cavity 28 through holes 34 in cover 30. By way of example, the pre-polymer mixture may include a monomer, such as isobornyl acrylate, a cross-linker and a photo-initiator. As is known, the pre-polymer mixture polymerizes and solidifies when exposed to a polymerizing agent such as ultraviolet light, temperature or the like. Optical mask 38 is then affixed to upper face 36 of cover 30, FIGS. 4 and 5. Optical mask 38 includes masking portion 40 having a shape corresponding to the desired configuration of channel network 42, FIG. 6, to be formed in microfluidic device 10, as hereinafter described. In order to accurately position optical mask 38 on upper face 36 of cover 30 of microfluidic device 10, optical mask 38 has a length L1 generally equal to the length L of cover 30 and a width W1 generally equal to the width W of cover 30. It can be appreciated that masking portion 40 of optical mask 38 shields a portion of the pre-polymer mixture in cavity 28 from the polymerizing agent directed at cover 30.

In order to form channel network 42, ultraviolet light is directed towards microfluidic device 10 at an angle generally perpendicular to upper face 36 of cover 30. It can be appreciated masking portion 40 of optical mask 38 shields a first portion of the pre-polymer mixture in cavity 28 the ultraviolet light. Non-masking portion 44 of optical mask 38 allows the ultraviolet light to pass therethrough such that a second portion of the pre-polymer mixture in cavity 28 is exposed to the ultraviolet light and polymerizes. As described, the portion of pre-polymer mixture shielded from the ultraviolet light defines a volume of pre-polymer mixture having a shape corresponding to the desired configuration of channel network 42 to be formed in microfluidic device 10. The volume of pre-polymer mixture not exposed to the ultraviolet light is flushed from the interior of microfluidic device 10 to form channel network 42. By way of example, channel network 42 includes a plurality of generally parallel, rectangular channels 42*a*, 42*b* and 42*c* having input ends 48 and output ends 50.

Referring to FIGS. 7 and 8, once channel network 42 is formed within microfluidic device 10, it is contemplated to form one or more hydrogel posts 52 in each channel 42*a*, 42*b* and 42*c* of channel network 42. Each hydrogel post 52 is formed by introducing pre-polymer mixture 43 into corresponding channels 42*a*, 42*b* and 42*c* in microfluidic device 10 through holes 34 in cover 30. By way of example, the pre-polymer mixture may include a monomer, such as polyacrylamide, a cross-linker and a photo-initiator. As is known, the pre-polymer mixture polymerizes when exposed to a polymerizing agent such as ultraviolet light, temperature or the like. Optical mask 54 is then affixed to upper face 36 of cover 30. Optical mask 54 includes non-masking portions 56 having diameters corresponding to predetermined, user desired diameters for hydrogel posts 52 to be formed in corresponding channels 42*a*, 42*b* and 42*c* of microfluidic device 10, as hereinafter described.

With optical mask 54 positioned on upper face 36 of cover 30, ultraviolet light is directed towards microfluidic device 10 at an angle generally perpendicular to upper face 36 of cover 30. It can be appreciated masking portion 57 of optical mask 54 shields a first portion of the pre-polymer mixture in corresponding channel 42*a*, 42*b* and 42*c* from the ultraviolet light. Non-masking portions 56 of optical mask 54 allow ultraviolet light to pass therethrough such that a second portion of the pre-polymer mixture in corresponding channel 42*a*, 42*b* and 42*c* is exposed to the ultraviolet light and polymerizes to form hydrogel posts 52. The volume of pre-polymer mixture not exposed to the ultraviolet light is flushed from corresponding channels 42*a*, 42*b* and 42*c* of microfluidic device 10 to leaving hydrogel posts 52 therein, FIG. 10.

Figure 11A:
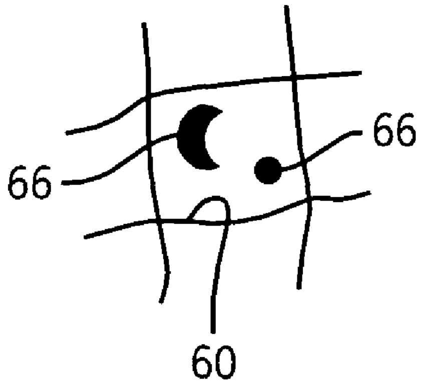
FIG. 11*a* is an enlarged, schematic view of a first embodiment of a hydrogel post.
Figure 11B:
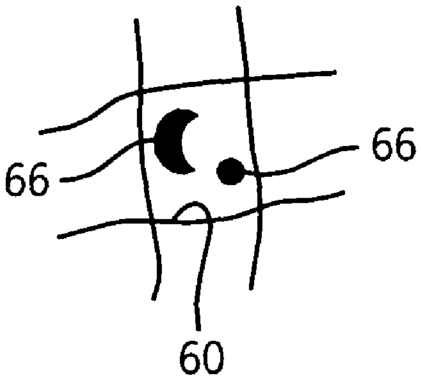
FIG. 11*b* is an enlarged, schematic diagram of a second embodiment of a hydrogel post.

As is known, in a hydrogel, the polymer chains are usually cross-linked in a random manner. These cross-links may be covalent bonds or electrostatic interactions (e.g. hydrogen bonds). In a simplified model, hydrogel post 52 can be represented as a network of pores 60 formed from intertwining and cross-linking of the polymer chains. As such, by choosing the appropriate composition of the pre-polymer mixture, one can control the size of pores 60, FIGS. 11*a-b*. For example, in a hydrogel post formed from a pre-polymer mixture including 7.5% of the polyacrylamide monomer, the average pore size of pores 60 in hydrogel post 52 is 50 Å, FIG. 11*a*. When the concentration of the polyacrylamide monomer in the pre-polymer mixture is increased to 10%, the average pore size of pores 60 in hydrogel post 52 will decrease below 50 Å, FIG. 11*b*.

Figure 12:
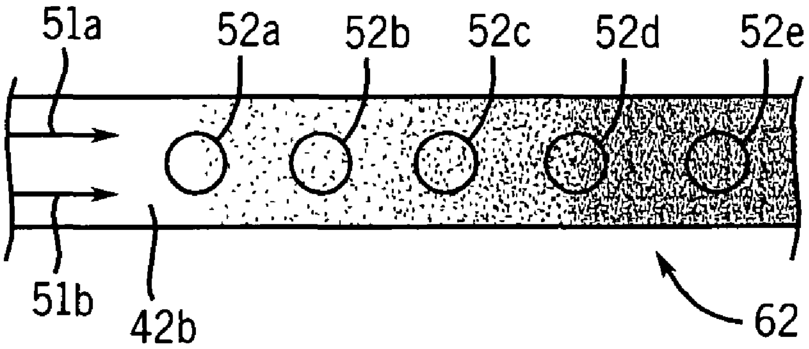
FIG. 12 is a schematic view showing an alternate methodology for the formation of the hydrogel posts in the channels of the microfluidic device.

Referring to FIG. 12, in order to create a series of hydrogel posts 52 in a corresponding channel 42*a*, 42*b* and 42*c* of microfluidic device 10 with varying monomer concentrations, it is contemplated to utilize the principles of laminar flow. More specifically, first and second streams 51*a* and 51*b*, respectively, of different pre-polymer mixtures may be introduced into a corresponding channel 42*a*, 42*b* and 42*c*. As first and second streams 51*a* and 51*b*, respectively, of different pre-polymer mixtures flow though corresponding channels 42*a*, 42*b* and 42*c*, first and second streams 51*a* and 51*b*, respectively, are allowed to mix by diffusion such that a concentration gradient in monomer concentration is created along the entire length of the corresponding channels 42*a*, 42*b* and 42*c*. Thereafter, the diffused pre-polymer mixtures may be polymerized, as heretofore described, so as to form a series of hydrogel posts 52*a*-52*e* with different nano-environments in the corresponding channels 42*a*, 42*b* and 42*c*. By providing a series of hydrogel posts 52*a*-52*e* with different nano-environments in each channel 42*a*, 42*b* and 42*c* of channel network 42, an array, generally designated by the reference numeral 62, of varying monomer concentration (shown by different shades) may be formed.

Further, it is contemplated to create a heterogeneous nano-environment within hydrogel post 52. As heretofore described, during liquid phase photo-polymerization of hydrogel posts 52, the ultraviolet light is irradiated from a single side of microfluidic device 10, namely, upper face 36 of cover 30. Since the rate and extent of polymerization depends on the intensity of the ultraviolet light, which can change with the depth of the corresponding channel 42*a*, 42*b* and 42*c*, hydrogel posts 52 with a heterogeneous environment may be formed.

With microfluidic device 10 fabricated, as heretofore described, it is contemplated to utilize microfluidic device 10 as a cell mimic platform for biomolecular studies. More specifically, hydrogel posts 52 may be used to mimic various properties within the interior of a cell. In operation, various streams of solution are sequentially introduced in channels 42*a*, 42*b* and 42*c*. Each stream includes predetermined probe molecules 66, FIGS. 11*a*-11*b*, such as proteins, reagents, chemicals, or the like. It can be appreciated that the polymer chains in hydrogel posts 52 occupy a certain volume and 'exclude' probe molecules from entering this space. This region is referred to as an excluded volume. However, it can be appreciated that molecules 66 in each stream can move into or between pores 60 in each hydrogel post 52 via diffusion.

The polymer network of each hydrogel post 52 that encloses a volume (i.e., pore 60) that contains non-polymeric molecules is referred to as a confining environment. The properties of probe molecules 66 entrapped are similar to the environment outside of pore 60. Alternatively, when polymer chains in each hydrogel post 52 are dissolved in the solution, as hereinafter described, a crowding environment results. The dissolved polymer chains compete for space (and hydration) with probe molecules 66. In other words, the region near the matrix of hydrophilic polymers is crowded due to 'dissolved' of polymer chains.

By choosing the appropriate composition of pre-polymer mixtures used to fabricate hydrogel posts 52, one can control the size of pores 60, and hence, the effects of confining and crowding therein. More specifically, in a bi-molecular reaction, the binding efficiency (at equilibrium) between molecules depends on the equilibrium dissociation constant ($K_d$), which is a function of the activities of the reactants ($a_r$) and products ($a_p$). The activity of a species is a function of its concentration in solution, with a multiplying factor (activity coefficient, γ) that depends on the extent of inter-species interaction. In a dilute solution, intermolecular interactions are negligible and the activity coefficients ($\gamma_p$, $\gamma_r$) can be approximated to unity, thus allowing one to equate activities to concentrations. The equilibrium dissociation constant of a reaction can then be approximated to the ratio of concentrations of reactants ($c_r$) and products ($c_p$). Since most biochemical reactions are carried out in dilute solution, the measured equilibrium dissociation constants ($K_{do}$) follow this approximation. However, in the case of a confined or crowded environment, the approximation does not hold and the actual equilibrium dissociation constant ($K_d$) differs from the measured value by the activity factor (Γ).

$$K_d = \frac{a_r}{a_p}\frac{c_r\gamma_r}{c_p\gamma_p} = K_{d0}\Gamma \quad \text{Equation 1}$$

For example, the interaction between molecules 66 within pore 60 of hydrogel post 52 is considered. As the concentration of the monomer (in the pre-polymer mixture) is increased, the size of pore 60 decreases, resulting in increased 'apparent' concentration, although the actual concentration inside hydrogel post 52 will be lower due to volume occupied by the polymer chains. An increase in apparent concentration will result in a higher collision rate and an increased probability that the molecules will interact. Moreover, the polymer chains of hydrogel posts 52 retard the transport of the molecules away from pore 60, thus further decreasing the apparent equilibrium dissociation constant. Therefore, as the size of pore 60 is decreased, a shift in the apparent equilibrium dissociation constant is expected. As the size of pore 60 becomes smaller, the nano-environment in hydrogel post 52 becomes crowded with the polymer chains competing for space.

There are two aspects of crowding that are significant. The first effect is on the equilibrium constant itself. The activity coefficient of a solute (reactant) species is related to the work required to insert a molecule of the species into the volume of interest. This work depends not only on the concentration of the background molecules and their shape, but also on their interactions (e.g., electrostatic) with the environment. The second effect of crowding is on the dynamics of the reactants. Simulation studies have shown that the dynamics of solutes can be drastically different even if their static properties are similar. This can be understood by noting that the work required to insert a molecule depends on the cavities available and the environment in the vicinities of these cavities. The dynamics of the species depends, in addition to the nature of the cavities, on their connectivity. These dynamic effects can have a strong effect on the experimentally observed behavior and are not reflected in the activity coefficients.

It can be appreciated that the environment inside hydrogel post 52 prepared from low monomer concentration (larger pore size) is confining, rather than crowded. To induce crowdedness, it is contemplated to photo-polymerize the pre-polymer mixture used to fabricate hydrogel post 52 in the presence of non-reactive, polyethylene glycol (PEG) chains. Specifically, low molecular PEG chains that are soluble in water are incorporated in the pre-polymer mixture. The PEG chains are trapped inside the cross-linked matrix during photo-polymerization, and contribute towards crowdedness. Low molecular weight PEG chains are more likely to be in open form (i.e. not globular) and are easily entangled in the matrix. Therefore, flow of the polymer chains out of hydrogel post 52 is minimal.

It can also be appreciated that charge or specific groups on the polymer matrix can interact with the proteins and thus affect binding between the proteins. To minimize this interaction, it is contemplated to form hydrogel post 52 from polyacrylamide and PEG polymers. These polymers are neutral and are unlikely to be involved in electrostatic interaction with the proteins. Specifically, PEG chains are well known for minimal interaction with proteins making them widely used as surface coating to prevent protein adsorption. Further, polyacrylamide is widely utilized in gel electrophoresis and its interaction with proteins is minimal. To verify that the proteins are not interacting in any way with the proteins, the extent of swelling (at equilibrium) of hydrogel post 52 may be measured in different protein solutions. If for a given protein, there is no correlation between swelling of post and protein concentration, then it is indicative that there is minimal interaction between the polymer and the protein.

By way of example, microfluidic device 10 may be used to study the interaction between *E. coli* sigma and core RNA polymerase. As is known, RNA polymerase is an enzyme that catalyzes the production of RNA from DNA, which then forms a template for protein production. Interaction between a sigma and core RNAP results in turning certain genes "on." In prokaryotes, there are different types of sigma proteins that turn on different sets of genes. Therefore, selectivity in binding the sigma proteins can change the gene expression of the bacterial cell. Similar strategies are found in eukaryotic cells and understanding the reactivity between these transcriptional proteins is important to characterize drug effects. The interaction between proteins can be quantified via fluorescence resonance energy transfer (FRET) as this detection technique allows for high throughput studies.

In FRET, both proteins are fluorescent labeled. The dyes are chosen such that the emission energy of one (the donor) overlaps with excitation energy of the second dye (the acceptor). The intensity of emission of the second dye varies as a function of the distance between the proteins. Thus, if the proteins are in close proximity, more resonance energy transfer will occur and higher acceptor intensity will be observed. The hydrogel posts 52 in channels 42*a*, 42*b* and 42*c* will be equilibrated with a mixture of labeled core (donor) and sigma (acceptor) proteins. The concentration of the donor in channels 42*a*, 42*b* and 42*c* is maintained constant, while the concentration of the acceptor protein will be varied. This variation in protein concentration will allow for the measurement of equilibrium dissociation constant ($K_d$) in the different microenvironments of hydrogel posts 52. Further, recording the interactions in hydrogel posts 52 with different monomer concentration will provide a library of interactions in cell mimics that represent various spatio-temporal states of a cell.

During operation, the $K_d$ within hydrogel 52 will change with increased monomer concentration (decreasing pore-size) and increased binding. However, at very high monomer concentration, a decrease in $K_d$ can be expected since the limited space inside the polymer matrix will not be able to accommodate the complex or individual proteins. A decrease in intensity of the FRET signal as the monomer concentration of the gel is increased. However, this change in intensity can be due to other events such as: fluorescence quenching at higher concentration of molecules in the crowded environment; lower number of molecules inside the polymer construct due to reduced diffusion; and increased interaction of biomolecules with polymer chains. Another factor that affects the intensity is the efficiency of labeling. The intensity will depend on the number of labels on the protein molecules. The number of fluorescent molecules per protein will be the same and is expected to be a Boltzman distribution. It is contemplated to optimize labeling the conditions so that only one dye is bound to a protein. Intensity data may be collected from a large number of samples and averaged.

For protein-protein interactions that already have a low equilibrium dissociation constant, the confining or crowding environment may not influence the binding. Since it is known that salt concentration can change the binding between sigma and core proteins, it is contemplated to increase salt concentration in the buffer to reduce the binding interaction so that a change can be measured. This 'tweaking' will be necessary to characterize the hydrogel environment as a potential cell mimic. The distribution of salt in polyacrylamide gel should be homogeneous because the hydrogels used to form hydrogel posts 52 are non-responsive and the gel is used in gel electrophoresis wherein protein is separated in different buffer conditions As described, a cell mimic platform is provided that includes microfluidic device 10 having channel network 42 housing hydrogel posts 52 (of varying composition) for high throughput protein studies. Hydrogel posts 52 mimic the crowded environment of the interior of a cell. The cell mimic platform may be used to characterize the effect of hydrogel nano-environment on protein interactions, namely, the binding between sigma and core RNA polymerase proteins inside hydrogel posts 52 via fluorescence resonance energy transfer. Channel network 42 of microfluidic device 10 allows for the efficient transport of proteins to hydrogel posts 52. As a result, the cell mimic platform of the present invention may be used in applications to characterize protein interactions in proteomics and in screening for drugs in pharmacology.

Various modes of carrying out the invention are contemplated as being within the scope of the following claims particularly pointing out and distinctly claiming the subject matter that is regarded as the invention.

We claim:

1. A method of mimicking the environment within a cell to compare molecule interactions, comprising the steps of:

providing a microfluidic device and positioning a first hydrogel post within the device, the first post defining a first environment within a pore therein;

depositing first and second molecules in the first environment;

monitoring the interaction of the first and second molecules in the first environment;

positioning a second hydrogel post within the device, the second post defining a second environment within a pore therein;

depositing third and fourth molecules in the second environment;

monitoring the interaction of the first and second molecules in the first environment and the third and fourth molecules in the second environment; and comparing the interaction of the first and second molecules with the interaction of the third and fourth molecules.

2. The method of claim 1 wherein the step of depositing the first and second molecules in the first environment includes the steps of:

introducing a stream of fluid having the first molecule into the microfluidic device; and allowing the first molecule to diffuse into the first pore.

3. The method of claim 2 wherein the step of depositing the second molecule in the second pore includes the steps of:

introducing a second stream of fluid having the second molecule into the microfluidic device; and allowing the second molecule to diffuse into the second pore.

4. The method of claim 1 comprising the additional step of fabricating the first post from a monomer, a cross-linker and a photo-initiator.

5. The method of claim 1 wherein the first environment has a first volume and the second environment has a second volume, the second volume being less than the first volume.

6. The method of claim 1 comprising the additional step of positioning an array of posts within the microfluidic device, the first and second posts being part of the array of posts in the microfluidic device.

7. The method of claim 1 wherein the first environment has a first volume and wherein the method comprises the additional step of varying the volume of the first environment.

* * * * *